United States Patent [19]
Kruse

[11] Patent Number: 4,749,717
[45] Date of Patent: Jun. 7, 1988

[54] DOPAMINE-BETA-HYDROXYLASE INHIBITORS

[75] Inventor: Lawrence I. Kruse, Haddonfield, N.J.

[73] Assignee: SmithKline Beckman Corporation, Philadelphia, Pa.

[21] Appl. No.: 1,282

[22] Filed: Jan. 8, 1987

[51] Int. Cl.$^4$ .................. A61K 31/415; C07D 409/06
[52] U.S. Cl. .................... 514/392; 514/397; 548/318; 548/336
[58] Field of Search ............... 548/318, 336; 514/392, 514/397

[56] References Cited

U.S. PATENT DOCUMENTS 4,634,711  1/1987  Kaiser et al. .................. 514/341

FOREIGN PATENT DOCUMENTS 60-4181  1/1985  Japan .................. 549/65

OTHER PUBLICATIONS

Chemical Abstracts 100:85629t(1984)[Belgodere, E., et al., Heterocycles 1983, 20(10), 2019-23].

Chemical Abstracts, 102:132034y(1985)[EP 125,033, Frazee et al., 11/14/84].

Blicke, F. in *Thiophene and its Derivatives* by H. D. Hartough, Interscience, New York, 1952, p. 29.

Bargar, T., et al., *J. Med. Chem.* 29:315 (1986).

Primary Examiner—Richard A. Schwartz
Attorney, Agent, or Firm—Vincent L. Fabiano; Stuart R. Suter; Alan D. Lourie

[57] ABSTRACT

Potent dopamine-β-hydroxylase inhibitors having the Formula

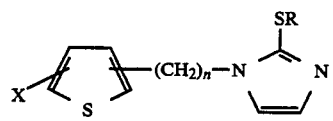

that are useful to inhibit dopamine-β-hydroxylase activity, pharmaceutical compositions including these inhibitors, and methods of using these inhibitors to inhibit dopamine-β-hydroxylase activity in mammals. Also disclosed are novel intermediates useful in preparing the presently invented inhibitors.

12 Claims, No Drawings

DOPAMINE-BETA-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409-432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179-192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylamine analogue may yield potent inhibitors.

Known DBH inhibitors include:

(a) 5-alkylpicolinic acids [See, Suda et al., *Chem. Pharm. Bull.* 17, 2377 (1969); Umezawa et al., *Bi-ochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];

(b) BRL 8242 [See Claxton et al., *Eur J. Pharmacol.* 37, 179 (1976)];

(c) 1-alkylimidazole-2-thiols [See, Hanlon et al., *Life Sci.* 12, 417 (1973); Fuller et al., *Adv. Enzyme Regul.* 15, 267 (1976)];

(d) substituted thioureas [See, Johnson et al., *J. Pharmacol. Exp. Ther.* 168, 229 (1969)]; and (e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylalamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5-(4-chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamine, is reported by Ehrreich et al., "New Antihypertensive Drugs", Spectrum Publications, 1976, pg. 409-432, to be a DBH inhibitor that has antihypertensive activity.

In European Patent Application No. 125,033 (published November 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

Recently, Skuballa, et al., discovered that certain heteroaromatic amines are DBH substrates and are potent, time-dependent DBH inhibitors. *J. Med. Chem.* 29:3, 315 (1986). Included among the heteroaromatic amines which inhibit DBH are three 2-(2-thienyl)-allylamines and 3-(2-thienyl)allylamine.

SUMMARY OF THE INVENTION

The present invention resides in the discovery that DBH is inhibited by substituted 1-(2- or 3-thienylalkyl-)imidazole-2-thiols and 1-(2- or 3-thienylalkyl)-2-alkyl-thioimidazoles. produce prolonged DBH inhibition.

Presently preferred compounds of the invention and compounds included in the pharmaceutical compositions and used in the methods of the invention include:
1-(2-thienylmethyl)imidazole-2-thiol; and
1-(3-thienylmethyl)imidazole-2-thiol.

In a further aspect of the invention there are provided novel intermediates useful in preparing substituted 1-(2- or 3-thienylalkyl)imidazole-2-thiols and 1-(2- or 3-thienylalkyl)alkylthioimidazoles.

The invention also is a method of inhibiting DBH activity in mammals, including humans, which comprises administering internally to a subject an effective amount of a substituted 1-(2- or 3-thienylalkyl)imidazole-2-thiol or 1-(2- or 3-thienylalkyl)-2-alkylthioimidazole.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

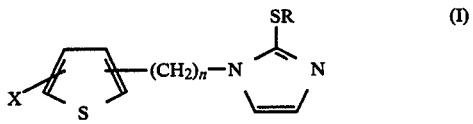

in which:

X is H, F, Cl, Br, I, $C_{1-4}$ alkyl, CN, $NO_2$, $SO_2NH_2$, COOH, CHO, $C_{1-4}$ alkoxy, $CH_2OH$, $CF_3$, $SO_2CH_3$, $SO_2CF_3$, or $CO_2C_aH_{2a+1}$ wherein a is 1-5, or any accessible combination thereof of up to 3 substituents; or n is 1-5;

R is hydrogen or $C_{1-4}$ alkyl; or any pharmaceutically acceptable salt or hydrate thereof.

As used herein, "accessible combination thereof" means any other combination of the substituents that is available by chemical synthesis and is stable and "$C_{1-4}$ alkyl" means a straight or branched hydrocarbon chain having from one to four carbon atoms.

It is intended that Formula I includes the tautomer of the compounds in which R is hydrogen, that is, compounds having the above formula wherein the imidazole moiety has either of the below formulae:

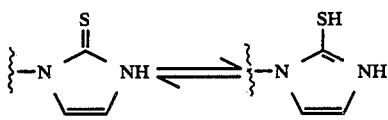

Formula (I) compounds are prepared from thiophenecarboxaldehyde or thienylalkylaldehydes by processes exemplified in Scheme I, below. The starting thiophenecarboxaldehyde and thienylalkylaldehydes are described in published references and can be purchased and readily prepared from available materials. In Scheme I, X and n are the same as in Formula (I).

Scheme I

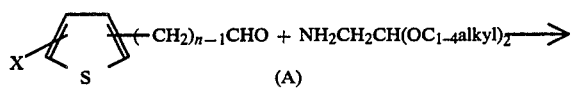

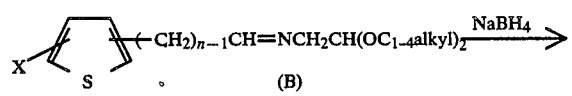

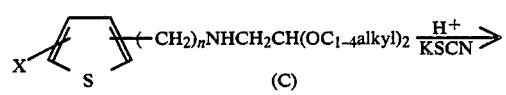

-continued
Scheme I

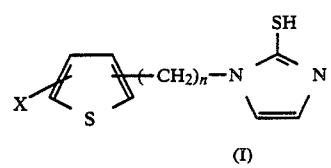

Scheme I illustrates reaction of thiophenecarboxaldehyde and thienylalkylaldehydes (A) with an aminoacetaldehyde di($C_{1-4}$ alkyl) acetal, preferably aminoacetaldehyde dimethyl acetal to form compounds of formula (B). This reaction is carried out by heating the reactants to 50° to 150° C., preferably 100° C., neat or in an inert organic solvent such as ethyl ether, tetrahydrofuran, various lower alkyl alcohols, dimethylformamide, or ethyl acetate.

Formula (B) compounds then are reduced using a suitable reducing agent such as diborane, borane, tetrahydrofuran, lithium aluminum hydride, hydrogen over platinum or palladium, or, preferably, sodium borohydride to prepare compounds of Formula (C).

Formula (I) compounds are prepared by reaction of formula (C) compounds with acidic thiocyanate, preferably potassium thiocyanate, in an inert organic solvent such as listed above, preferably an aqueous $C_{1-4}$ alkyl alcohol.

Compounds of the invention in which R is $C_{1-4}$ alkyl are prepared by alkylating the corresponding Formula (I) compound with an alkyl halide, for example, methyl iodide in methanol, by known procedures. Other alkyl halides such as methyl bromide or methyl chloride, in appropriate solvents, can be substituted for methyl iodide. Further, the compounds in which R is an alkyl group other than methyl are prepared by reacting the corresponding Formula (I) compound with an alkyl halide, such as butyl iodide, in an appropriate solvent to yield the desired substituted 1-(2- or 3-thienylalkyl)-2-alkylthioimidazole of the invention.

In preparing the presently invented compounds of Formula I, novel intermediate compounds of the following formula were synthesized:

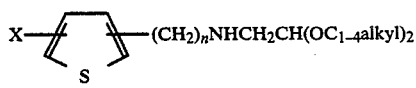

in which:

X is H, F, Cl, Br, I, $C_{1-4}$ alkyl, CN, $NO_2$, $SO_2 NH_2$, COOH, CHO, $C_{1-4}$ alkoxy, $CH_2OH$, $CF_3$, $SO_2 CH_3$, $SO_2CF_3$, or $CO_2C_aH_{2a+1}$ wherein a is 1-5, or any accessible combination thereof of up to 3 substituents; and n is 1-5.

The pharmaceutically acceptable acid addition salts of compounds of the invention are formed with strong or moderately strong organic or inorganic acids by methods known to the art. For example, the base is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Because the Formula I compounds inhibit DBH activity, they have therapeutic value as diuretic, natriuretic, cardiotonic, antihypertensive, and vasodilator agents, as well as antiulcerogenic and anti-Parkinson in agents. Listed in Table I are the compounds of the invention that were tested for in vitro DBH inhibition by a standard procedure for assaying conversion of tyramine to octopamine in the presence of DBH. J. J. Pisano, et al., *Biochim. Biophys. Acta*, 43, 566–568 (1960). Octopamine was assayed following sodium periodate oxidation to p-hydroxybenzaldehyde by measuring spectrophotometric absorbance at 330 nm. In Table I, inhibition is given in micromolar concentration of compound at which DBH activity was halved IC50) By this test, fusaric acid had an $IC_{50}$ of 0.8 micromolar.

TABLE I

| Compound | DBH $IC_{50}(\mu M)$ |
| --- | --- |
| 1-(2-thienylmethyl)imidazole-2-thiol | 13 |
| 1-(3-thienylmethyl)imidazole-2-thiol | 7.4 |

Further, spontaneously hypertensive rats were treated with a suspension or solution of 1-(2-thienylmethyl)imidazole-2-thiol at a dose of 50 mg/kg intraperitoneally, and mean arterial blood pressure was monitored for 260 minutes using indwelling cannulae in the tail arteries. When compared to vehicle-treated controls, animals treated with the compound of the invention exhibited significant blood pressure reductions within 60 minutes after treatment. The maximal blood pressure reduction was approximately 25 to 30 mmHg.

The compounds of Formula I can be incorporated into convenient pharmaceutical dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical compositions are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula I in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, or continuously by infusion. Oral dosage units for human administration preferably contain from 1 to 500 mg of active compound. Parenteral administration, which generally requires lower dosages also can be used. Oral administration, at higher dosages, however, can be used when safe and convenient for the patient.

The method of this invention of inhibiting DBH activity in mammals, including humans, comprises administering internally to a subject in need of such inhibition an effective DBH inhibiting amount of a compound of Formula I.

The following examples are illustrative of preparation of Formula I compounds. The examples are not intended to limit the scope of the invention as defined hereinabove and as claimed below.

EXAMPLE 1

1-(2-Thienylmethyl)Imidazole-2-Thiol

A mixture of aminoacetaldehyde dimethylacetal (5.45 ml., 0.05 mole) and 2-thiophenecarboxaldehyde (4.67 ml., 0.05 mole) was heated at 100° C. for 2 hours and the reaction mixture was cooled in ice and diluted with ethyl alcohol (50 ml.). Sodium borohydride (1 g) was added to the solution and the reaction mixture was stirred for 17 hours. The solvent was removed under vacuum, ethyl acetate (50ml) was added, and the solution was washed with water and brine and dried over sodium sulfate. The mixture was filtered and the solvent was removed under vacuum. The resultant oil was diluted with ethyl alcohol (69 ml), potassium thiocyanate (5.59 g, 0.0575 mole) in water (115 ml) followed by concentrated hydrochloric acid (11.5 ml) and the solution was heated at reflux for 2.5 hours. The solvent was removed until an oil came out of solution at which point the reaction mixture was cooled with ice, diluted with water, and the crude product was filtered. The product was first recrystallized from a mixture of ethyl acetate-hexane followed by ethyl acetate to give 1-(2-thienylmethyl)imidazole-2-thiol, melting at 130°–131° C. (2.79 g., 28%).

EXAMPLE 2

1-(3-Thienylmethyl)imidazole-2-thiol

The procedure of Example 1, beginning with 3-thiophenecarboxaldehyde yielded 1-(3-thienylmethyl)imidazole-2-thiol, melting at 130°–131° C. (3.10 g., 32%).

EXAMPLE 3

1-(2-Thienylmethyl)-2-methylthioimidazole

Reaction of 1-(2-thienylmethyl)imidazole-2-thiol, prepared as in Example 1, with methyl iodide and sodium methoxide in methanol by standard techniques yields 1-(2-thienylmethyl)-2-methylthioimidazole.

EXAMPLE 4

1-(2-Thienylpropyl)imidazole-2-thiol

The process of Example 1 wherein 2-thiophenecarboxaldehyde is replaced by 2-thienylpropanaldehyde yields 1-(2-thienylpropyl)imidazole-2-thiol.

EXAMPLE 5

1-(2-Thienylethyl)imidazole-2-thiol

The process of Example 1 wherein 2-thiophenecarboxaldehyde is replaced by 2-thienylacetaldehyde yields 1-(2-thienylethyl)imidazole-2-thiol.

EXAMPLE 6

1-(3-Fluoro-2-thienylmethyl)imidazole-2-thiol

The process of Example 1 wherein 2-thiophenecarboxaldehyde is replaced by 3-fluoro-2-thiophenecarboxaldehyde yields 1-(3-fluoro-2-thienylmethyl)imidazole-2-thiol.

EXAMPLE 7

1-(4-Methyl-2-thienylmethyl)imidazole-2-thiol

The process of Example 1 wherein 2-thiophenecarboxaldehyde is replaced by 4-methyl-2-thiophenecarboxaldehyde yields 1-(4-methyl-2-thienylmethyl)-imidazole-2-thiol.

EXAMPLE 8

1-(5-Nitro-2-thienylmethyl)imidazole-2-thiol

The process of Example 1 wherein 2-thiophenecarboxaldehyde is replaced by 5-nitro-2-thiophenecarboxaldehyde yields 1-(5-nitro-2-thienylmethyl)-imidazole-2-thiol.

EXAMPLE 9

1-(3-Ethoxy-2-thienylmethyl)imidazole-2-thiol

The process of Example 1 wherein 2-thiophenecarboxaldehyde is replaced by 3-ethoxy-2-thiophenemethylcarboxaldehyde yields 1-(3-ethoxy-2-thienylmethyl)imidazole-2-thiol.

EXAMPLE 10

1-(4-Acetoxy-2-thienylmethyl)imidazole-2-thiol

The process of Example 1 wherein 2-thiophenecarboxaldehyde is replaced by 4-acetoxy-2-thiophenemethylcarboxaldehyde yields 1-(4-acetoxy-2-thienylmethyl)-imidazole-2-thiol.

EXAMPLE 11

An oral dosage form for administering the presently invented compounds is produced by screening, mixing, and filling into hard gelatin capsules the ingredients in the proportions shown in Table III, below.

TABLE III

| Ingredients | Amounts |
|---|---|
| 1-(2-Thienylmethyl)imidazole-2-thiol | 50 mg |
| magnesium stearate | 5 mg |
| lactose | 75 mg |

EXAMPLE 12

The sucrose, calcium sulfate dihydrate, and Formula I compound shown in Table IV below, are mixed and granulated in the proportions shown with a 10% gelatin solution. The wet granules are screened, dried, mixed with the starch, talc and stearic acid, screened and compressed into a tablet.

TABLE IV

| Ingredients | Amounts |
|---|---|
| 1-(3-Thienylmethyl)imidazole-2-thiol | 100 mg |
| calcium sulfate dihydrate | 150 mg |
| sucrose | 20 mg |
| starch | 10 mg |
| talc | 5 mg |
| stearic acid | 3 mg |

EXAMPLE 18

1-(3-Thienylmethyl)imidazole-2-thiol hydrochloride, 75 mg, is dispursed in 25 ml of normal saline to prepare an injectable preparation.

While the preferred embodiments of the invention are illustrated by the above, the invention is not limited to the precise instructions herein disclosed and that the right to all modifications coming within the scope of the following claims and all equivalents thereof is reserved.

What is claimed is:

1. A compound represented by the formula:

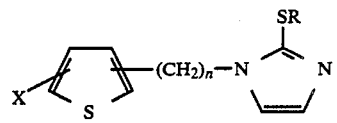

in which:

X is H, F, Cl, Br, I, $C_{1-4}$ alkyl, CN, $NO_2$, $SO_2NH_2$, COOH, CHO, $C_{1-4}$ alkoxy, $CH_2OH$, $CF_3$, $SO_2CH_3$, $SO_2CF_3$, or $CO_2C_aH_{2a+1}$ wherein $a$ is 1–5, or any accessible combination thereof of up to 3 substituents, R is H or $C_{1-4}$ alkyl, and n is 1–5; or any pharmaceutically acceptable salt or hydrate thereof, except compounds in which X and R are H, n is 1 and $(CH_2)_n$ is at the 2 position of the thiphene ring.

2. A compound of claim 1 wherein n is 1.
3. A compound of claim 2 wherein R is H.
4. A compound of claim 3 wherein $(CH_2)_n$ is at the 2 position of the thiophene ring.
5. A compound of claim 3 wherein $(CH_2)_n$ is at the 3 position of the thiophene ring.
6. A compound of claim 5 that is 1-(3-thienylmethyl) imidazole-2-thiol.
7. A pharmaceutical composition having dopamine-β-hydroxylase inhibiting activity in a dosage unit form comprising a pharmaceutical carrier and a compound represented by the formula:

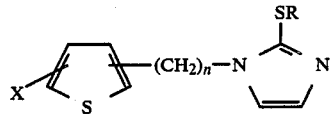

in which:

X is H, F, Cl, Br, I, $C_{1-4}$ alkyl, CN, $NO_2$, $SO_2NH_2$, COOH, CHO, $C_{1-4}$ alkoxy, $CH_2OH$, $CF_3$, $SO_2CH_3$, $SO_2CF_3$, or $CO_2C_aH_{2a+1}$ wherein $a$ is 1–5, or any accessible combination thereof of up to 3 substituents, R is H or $C_{1-4}$ alkyl, and n is 1–5; or any pharmaceutically acceptable salt or hydrate thereof.

8. A composition of claim 7 in which the compound is 1-(2-thienylmethyl) imidazole-2-thiol.
9. A composition of claim 7 in which the compound is 1-(3-thienylmethyl)imidazole-2-thiol.
10. A method of inhibiting dopamine-β-hydroxylase activity in mammals that comprises administering internally to a subject in need of such inhibition an effective amount of a compound represented by the formula:

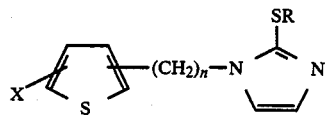

in which:

X is H, F, Cl, Br, I, $C_{1-4}$ alkyl, CN, $NO_2$, $SO_2NH_2$, COOH, CHO, $C_{1-4}$ alkoxy, $CH_2OH$, $CF_3$, $SO_2$, $CH_3$, $SO_2CF_3$, or $CO_2C_\alpha H_{2\alpha+1}$ wherein $\alpha$ is 1-5, or any accessible combination thereof of up to 3 substituents, R is H or $C_{1-4}$ alkyl, and n is 1-5; or any pharmaceutically acceptable salt or hydrate thereof.

11. The method of claim 10 in which the compound is 1-(2-thienylmethyl)imidazole-2-thiol.

12. The method of claim 10 in which the compound 1-(3-thienylmethyl)imidazole-2-thiol.

* * * * *